US009226723B2

United States Patent
Shi et al.

(10) Patent No.: US 9,226,723 B2
(45) Date of Patent: Jan. 5, 2016

(54) ORDERED SUBSET SCHEME IN SPECTRAL CT

(71) Applicants: Kabushiki Kaisha Toshiba, Minato-ku (JP); Toshiba Medical Systems Corporation, Otawara-shi (JP)

(72) Inventors: Daxin Shi, Buffalo Grove, IL (US); Yu Zou, Naperville, IL (US); Zhou Yu, Palatine, IL (US)

(73) Assignees: KABUSHIKI KAISHA TOSHIBA, Minato-ku (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 136 days.

(21) Appl. No.: 14/189,790

(22) Filed: Feb. 25, 2014

(65) Prior Publication Data
US 2015/0238157 A1     Aug. 27, 2015

(51) Int. Cl.
| G06K 9/00 | (2006.01) |
| A61B 6/00 | (2006.01) |
| A61B 6/03 | (2006.01) |
| G06T 7/00 | (2006.01) |
| G06T 5/00 | (2006.01) |

(52) U.S. Cl.
CPC ............. *A61B 6/5205* (2013.01); *A61B 6/032* (2013.01); *G06T 5/001* (2013.01); *G06T 7/0012* (2013.01); *G06T 2207/10072* (2013.01)

(58) Field of Classification Search
None
See application file for complete search history.

(56) References Cited

U.S. PATENT DOCUMENTS

| 5,748,705 A   * | 5/1998  | Stein et al. ................... 378/196 |
| 6,507,633 B1  * | 1/2003  | Elbakri et al. .................... 378/8 |
| 2003/0156684 A1* | 8/2003 | Fessler .......................... 378/210 |
| 2010/0189212 A1* | 7/2010 | Zou ................................. 378/5 |
| 2011/0164031 A1* | 7/2011 | Shi ................................. 345/419 |
| 2011/0280458 A1* | 11/2011 | Flohr et al. .................... 382/131 |
| 2012/0106816 A1* | 5/2012 | Bernard De Man et al. . 382/131 |
| 2012/0128265 A1* | 5/2012 | Silver et al. ................... 382/275 |

OTHER PUBLICATIONS

Hudson and Larkin, "Accelerated Image Reconstruction Using Ordered Subsets of Projection Data", IEEE Transactions on Medical Imaging, vol. 13, 1994, pp. 601-609.

* cited by examiner

*Primary Examiner* — Sumati Lefkowitz
*Assistant Examiner* — Carol Wang
(74) *Attorney, Agent, or Firm* — Oblon, McClelland, Maier & Neustadt, L.L.P.

(57) ABSTRACT

A spectral computed tomography (CT) ordered subsets (OS) reconstruction method using two sets of projection data having a different number of views is provided. The method includes obtaining a first set of projection data that includes single-energy CT data for a first number of views, obtaining a second set of projection data that includes spectral CT data for a second number of views, wherein the first and second numbers are integers and the second number is smaller than the first number, partitioning the first set of projection data into N equal-sized subsets of projection data, including the second set of projection data in each of the N subsets of projection data to generate N expanded subsets of projection data, and performing OS reconstruction with the N expanded subsets of projection data to generate a reconstructed CT image.

13 Claims, 8 Drawing Sheets

$$\begin{bmatrix} 1 \\ 6 \\ \cdot \\ \cdot \\ 71 \\ 1 \\ 81 \\ \cdot \\ \cdot \\ 1121 \end{bmatrix} \begin{bmatrix} 2 \\ 7 \\ \cdot \\ \cdot \\ 72 \\ 17 \\ 97 \\ \cdot \\ \cdot \\ 1137 \end{bmatrix} \cdots \begin{bmatrix} 5 \\ 10 \\ \cdot \\ \cdot \\ 75 \\ 65 \\ 145 \\ \cdot \\ \cdot \\ 1185 \end{bmatrix}$$

FIG. 5

ORDERED SUBSET SCHEME IN SPECTRAL CT

FIELD

Embodiments disclosed herein generally relate to computed tomography (CT) imaging. In particular, embodiments disclosed herein relate to a system and an associated method to perform ordered subsets reconstruction for sparsely distributed stationary detectors with a rotating X-ray source.

BACKGROUND

Radiographic imaging, in its simplest expression, is an X-ray beam traversing an object and a detector relating the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low energy X-ray from the generator, the details of the geometry and characteristics of the detector, and the capacity of the acquisition system are all elements that affect how the actual reconstruction is performed. In the reconstruction, the map of the linear attenuation coefficient (LAC) of the imaged subjects is obtained from the line integrals of the LAC through an inverse Radon transform. The line integrals can be related to the logarithm of the primary intensity of the X-rays passing through the subject.

A third-generation CT system can include sparsely distributed fourth-generation, photon-counting detectors. In such a combined system, the fourth-generation detectors collect primary beams through a range of detector fan angles.

In spectral CT, with combined $3^{rd}$- and $4^{th}$-generation geometries, two datasets from the $3^{rd}$- and $4^{th}$-generation detectors having different numbers of projection views are involved in the reconstruction problem. No methods are known for using the ordered subsets (OS) methodology for this specific reconstruction problem. The conventional OS scheme cannot be directly applied to this spectral CT reconstruction problem to gain speedup because two sets of data having different numbers of projection views are involved, one set containing a sparse number of views and the other set containing a dense number of views.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 3-5 illustrate various partitions of projection data;

DETAILED DESCRIPTION

Figure 1:
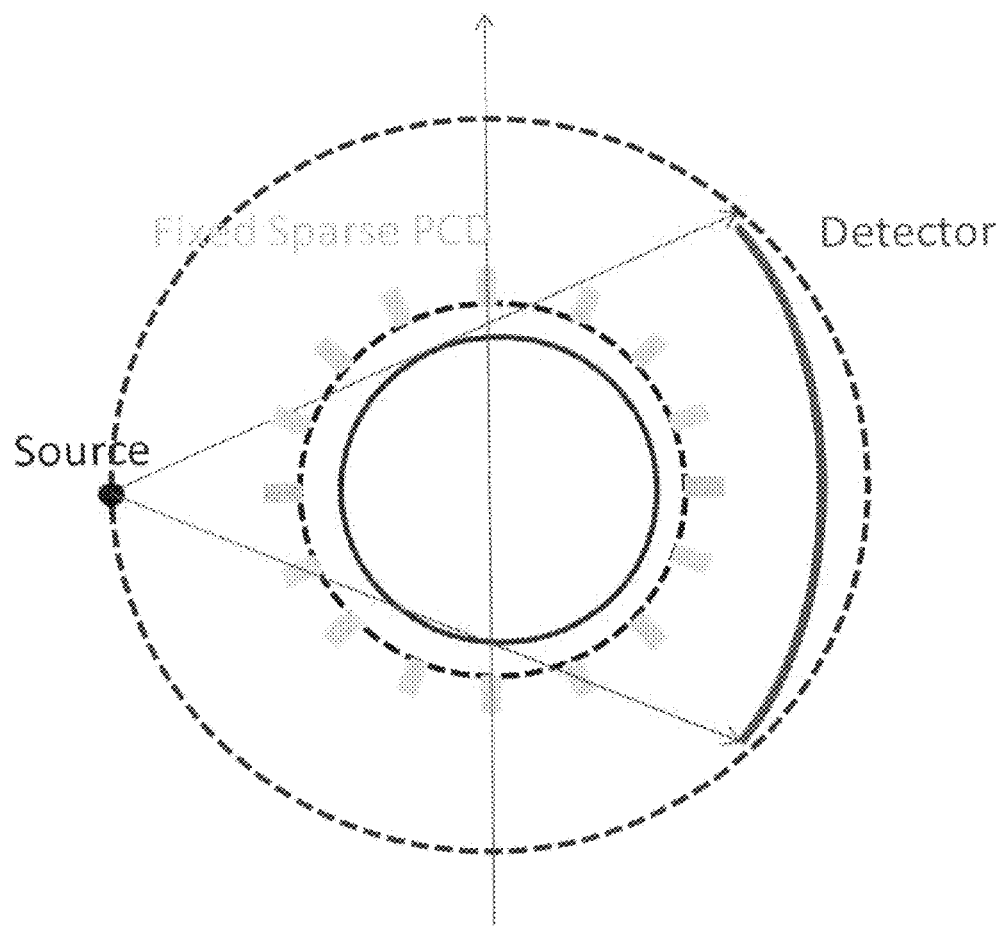
FIG. 1 illustrates a CT scanner apparatus including fixed photon-counting detectors, a rotating X-ray source, and third-generation detectors.

Embodiments described herein are directed to a new system and method for spectral computed tomography (CT) ordered subsets (OS) reconstruction.

In particular, in one embodiment, there is provided spectral computed tomography (CT) ordered subsets (OS) reconstruction method using two sets of projection data having a different number of views, the method comprising: (1) obtaining a first set of projection data that includes single-energy CT data for a first number of views; (2) obtaining a second set of projection data that includes spectral CT data for a second number of views, wherein the first and second numbers are integers and the second number is smaller than the first number; (3) partitioning the first set of projection data into N equal-sized subsets of projection data; (4) including the second set of projection data in each of the N subsets of projection data to generate N expanded subsets of projection data; and (5) performing OS reconstruction with the N expanded subsets of projection data to generate a reconstructed CT image.

In one embodiment, the method further comprises: (1) performing data domain decomposition on the second set of projection data to obtain measured basis line integrals; and (3) initializing basis images.

In another embodiment, the step of performing OS reconstruction comprises: (1) reprojecting the basis images to obtain first basis line integrals, and reprojecting the basis images to obtain second basis line integrals; (2) performing beam hardening correction on the first set of projection data to generate corrected data; (3) updating the basis images with a difference of the measured basis line integrals and the first basis line integrals and a difference of the corrected data and combined second basis line integrals; and (4) repeating the reprojecting, performing, and updating steps for the second number of views and for each of the N subsets;

In another embodiment, the method includes repeating the reprojecting, performing, updating steps, and repeating steps until predetermined convergence criteria is met.

In another embodiment, the partitioning step comprises partitioning the first set of projection data into N subsets of projection data, wherein N is set to be equal to the first number divided by the second number.

In another embodiment, the updating step comprises calculating a diagonal denominator matrix $D_n$ for each of the N subsets as $\text{Diag}\{D_n\} = NA^t_n W_n A_n 1$, wherein $A_n$ is a projector matrix, $W_n$ is a weighting matrix, t represents transpose, and 1 is a vector of ones.

In another embodiment, the method further comprises calculating a global matrix D as $$D_{ii} = \max_n D_{n,ii}.$$

In another embodiment, the updating step comprises calculating a diagonal denominator matrix D as $\text{Diag}\{D\} = A^t W^\sim A 1$, wherein A is a projector matrix, t represents transpose, and 1 is a vector of ones, and $W^\sim$ is a statistical weighting matrix that is calculated as $W^\sim_i = I_i \exp(-g^\sim_i)$ where $I_i$ is a flux for ray i and $g^\sim_i$ is a shadow-corrected attenuation.

In another embodiment, there is provided an apparatus to perform a spectral computed tomography (CT) ordered subsets (OS) reconstruction method using two sets of projection data having a different number of views, the apparatus comprising a processing circuit configured to (1) obtain a first set of projection data that includes single-energy CT data for a first number of views; (2) obtain a second set of projection data that includes spectral CT data for a second number of views, wherein the first and second numbers are integers and the second number is smaller than the first number; (3) partition the first set of projection data into N equal-sized subsets of projection data; (4) include the second set of projection data in each of the N subsets of projection data to generate N expanded subsets of projection data; and (5) perform OS reconstruction with the N expanded subsets of projection data to generate a reconstructed CT image.

Turning now to the drawings, FIG. 1 illustrates a combine third/fourth generation system having stationary, sparsely distributed fourth-generation detectors, along with a rotating third-generation source/detector system. The present reconstruction method can be used to process projection data obtained from the system shown in FIG. 1, but can also be used to process data obtained from other spectral CT scanner geometries.

Figure 2:
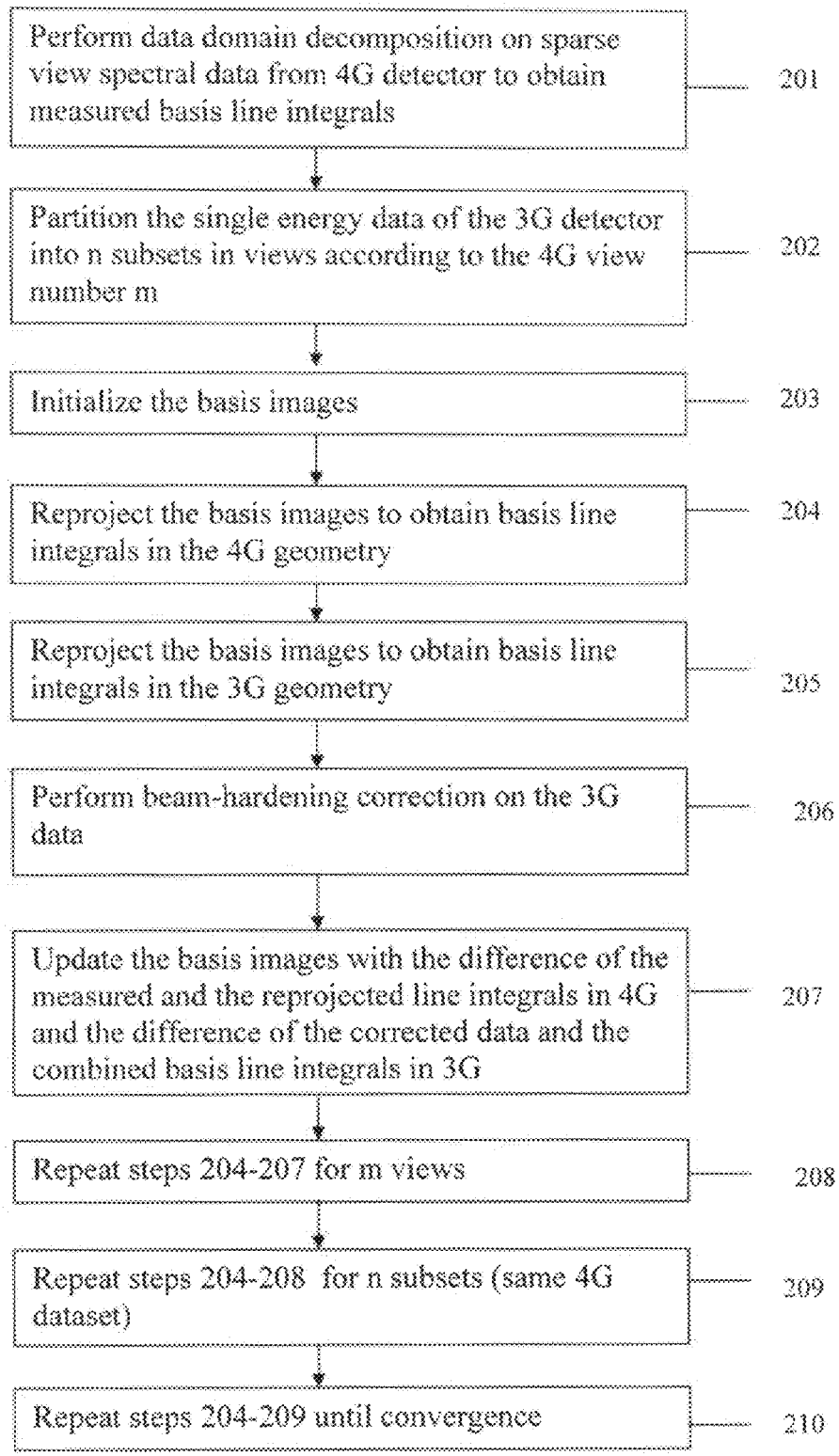
FIG. 2 illustrates a reconstruction method of the present embodiments.

FIG. 2 illustrates a flowchart for a reconstruction method for a spectral CT system according to one embodiment.

In step 201, data domain decomposition is performed on the sparse-view spectral data from the $4^{th}$-generation detector to obtain measured basis line integrals. One example method of performing the data domain decomposition is set forth in Y. Zou and M. D. Silver, "Analysis of fast kV-switching in dual energy CT using a pre-reconstruction decomposition technique," in Proc. SPIE 6913, Medical Imaging 2008: Phys. Med. Im., 2008, 691313:1-12, the contents of which are incorporated herein by reference.

In step 202, the single energy data of the $3^{rd}$-generation detector is partitioned into n subsets in views according to the $4^{th}$-generation view numbers.

For example, suppose dataset #2 contains 75 views and dataset #1 contains 1200 views. The 75-view data are coupled with the 1200-view data for image reconstructions. In this step, the 1200-view dataset #1 is partitioned into subsets, each of which contains 75 views, resulting in 16 subsets. The 75-view dataset #2 is coupled with each subset of 75 views from dataset #1 to form overall subsets. In this embodiment, the image reconstructed from one overall subset is fed into the next overall subset, and a total of sixteen overall subsets are visited sequentially to form one iteration.

Figure 3:
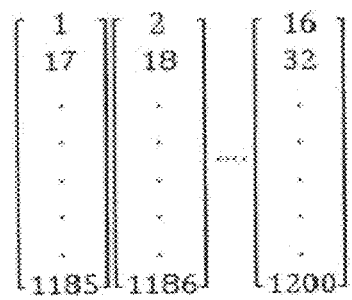

FIG. 3 illustrates the partitioning in the conventional ordered subsets scheme, again assuming 1200 views, which are partitioned into 16 groups, each of which contains 75 views. Each column forms one subset containing 75 views. Note that the number views in dataset #2 (in this example 75) does not have to be the same as the size of each partitioned group. For example, the 1200 views could be partitioned into 12 groups of 100-views each. However, the size of each group can be chosen to optimize parallel computing.

In the present embodiments, in one example, there are two sets of data, one that contains 1200 views and another that contains 75 views. In this step, the second data set is replicated and the first data set is partitioned in a conventional way and combined with the second data set, as shown in FIG. 4.

Figure 4:
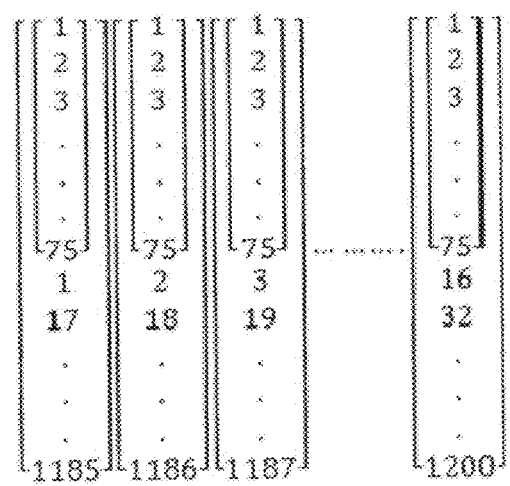

Each of the compound columns shown in FIG. 4 forms an overall subset. In each overall subset, we can further employ the conventional OS scheme to speed up image reconstruction, e.g., each overall subset can be partitioned further to form sub-subsets. For example, each overall subset can be grouped into five sub-subsets, each containing fifteen views. For example, FIG. 5 illustrates a sub-partition for the first overall subset shown in FIG. 4.

In the reconstruction method, a cost function can be defined as:

$$\psi(c) = \sum_{jn} \frac{1}{\sigma_{jn}^2} \left( \sum_i a_{ji} c_n(i) - L_n^{(M)}(j) \right)^2 + \sum_j \frac{1}{\sigma_j^2} \left( \sum_{n=1}^N L_n(j) \bar{\mu}_{nM} - g_M(j) - g_M^{(BH)}(L) \right)^2 + wV(c)$$

where $$L_n(j) = \sum_i A_{ji} c_n(i)$$

and $a_{ji}$: system matrix for 4th generation
$A_{ji}$: system matrix for 3rd generation
$c_n(i)$: basis images (e.g. water or bone).
$V(c)$: regularization. (w=0)
$g_M(j)$: measured 3rd-generation data.
$g_M^{(BH)}(L)$: beam hardening correction.
$L_n^{(M)}(j)$: 4th-generation data after decomposition.
$\bar{\mu}_{nM}$: average linear attenuation coefficient of material n over spectrum M.
$\sigma_{jn}^2$: variance of $L_n^{(M)}(j)$.
$\sigma_j^2$: variance of $g_M(j)$.

Other cost functions can be used with the present embodiments.

In step 203, the basis images are initialized. In particular, $c_n^{(0)}(i)=0$, where n represents water or bone, i runs over all images. Note that other initializations are possible, e.g., with FPB segments of bone and water.

In step 204, the basis images are reprojected to obtain basis line integrals in the $4^{th}$-generation geometry. In particular, the following sum is calculated:

$$\sum_i a_{ji} c_n(i)$$

where the index j indicates a ray.

In step 205, the basis image is reprojected to obtain basis line integrals in the $3^{rd}$-generation geometry. In particular, the following is calculated:

$$L_n(j) = \sum_i A_{ji} c_n(i).$$

In step 206, beam-hardening correction is performed on the $3^{rd}$-generation data to generate corrected data. In particular, $g_M^{(BH)}(L)$ is calculated by interpolation from a beam-hardening table, where the vector L is defined as:

$$L = \begin{pmatrix} L_{water}(j) \\ L_{Bone}(j) \end{pmatrix}.$$

In step 207, the basis images are updated with the difference of the measured and reprojected line integrals in $4^{th}$-generation geometry, and the difference of the corrected data from the beam-hardening step and the combined basis line integrals in the $3^{rd}$-generation geometry. In particular:

$$c_n(i) = c_n^{(0)}(i) - \frac{\frac{\partial \psi(c^{(0)})}{\partial c_n(i)}}{\sum_{i'n'} \frac{\partial^2 \psi(c^{(0)})}{\partial c_n(i) \partial c_{n'}(i')}},$$

where $$\frac{\partial \psi(c)}{\partial c_{n'}(i')} = \sum_{jn} \frac{2}{\sigma_{jn}^2} \left( \sum_i a_{ji} c_n(i) - L_n^{(M)}(j) \right) a_{ji'} \delta_{nn'} +$$

$$\sum_{jm} \frac{2}{\sigma_{jm}^2} \left( \sum_{n=1}^N L_n(j) \bar{\mu}_{nm} - g_m(j) - g_m^{(BH)}(L) \right) A_{ji'} \bar{\mu}_{n'm} + w \frac{\partial V(c)}{\partial c_{n'}(i')}$$

$$\frac{\partial^2 \psi(c)}{\partial c_n(i) \partial c_{n'}(i')} = \sum_j \frac{2}{\sigma_{jn}^2} a_{ji} a_{ji'} \delta_{nn'} +$$

$$\sum_{jm} \frac{2}{\sigma_{jm}^2} A_{ji} \bar{\mu}_{nm} A_{ji'} \bar{\mu}_{n'm} + w \frac{\partial^2 V(c)}{\partial c_n(i) \partial c_{n'}(i')}$$

In step 207, when there is missing data, the following method can be used.

Consider a cost function:

$$f(x) = \frac{1}{2} \|Ax - g\|_W^2.$$

In the OS method, we divide the data into N equally distributed subsets, and form a subset cost function $$f_n(x) = \frac{1}{2} \|A_n x - g_n\|_{W_n}^2$$

where n is the subset index. The subset cost functions are then minimized sequentially. The underlining assumption of the OS method is that the gradients of the subset cost function are approximately equal for all subsets. This assumption is generally true for the conventional geometry of CT systems. However, this assumption does not hold in the scenarios of missing data. For example, in the truncated region, pixels do not have full 360 degree samples. Another example is in the $4^{th}$-generation inner ring design of photon-counting CT systems where the shadows of the $4^{th}$-generation detectors block X-rays, causing missing data. These missing data are not uniformly distributed across all subsets, causing the assumption to break. In such cases, a naive application of OS method might not yield convergent results.

The conventional OS update equation is given by $$x \leftarrow x - ND^{-1} \nabla f_n(x) \tag{1}$$

where the denominator D is a diagonal matrix computed by $$\text{Diag}\{D\} = A^t W A 1, \tag{2}$$

in which 1 is a vector of all 1s. To improve the robustness of the OS method, we would like to ensure $$\text{Diag}\{D\} \geq NH_n, \tag{3}$$

where $NH_n$ is the Hessian of the nth subset, and N is the total number of subsets. In conventional CT geometry, this condition holds true approximately using equation (2). However, when missing data occurs, W will have many zero or near-zero entries that are not balanced among the subsets, which will break the condition in equation (3).

Note that in terms of the cost function disclosed above, the matrix D in equation (1) has diagonal elements given by $$D(ni) = \sum_{i'n'} \frac{\partial^2 \psi(c^{(0)})}{\partial c_n(i) \partial c_{n'}(i')}$$

In the present embodiments, in order to improve the robustness of the OS algorithm, several methods are used to modify the denominator D of the update equation so that the condition (3) holds approximately. Here, three new methods to compute D are used.

In the first method, we compute a diagonal matrix $D_n$ for each subset using $$\text{Diag}\{D_n\} = NA_n^t W_n A_n 1 \tag{4}$$

where $A_n$ and $W_n$ represent the projector and weighting matrix for each subset. One can prove that, in this formula, the condition in equation (3) holds. One drawback of this method is the additional memory requirement to save $D_n$ for each subset. The following two methods are used to address this problem.

In the second method, we can compute $D_n$ as in equation (4) and then compute a global D matrix using a max operation, that is, $$D_{ii} = \max_n D_{n,ii} \tag{5}$$

One can easily see that this method will also guarantee that condition (3) holds, since it is greater than all $D_n$ in the first method.

In the third method, we compute a new weighting matrix $\overline{W}$. $\overline{W}$ corresponds to a statistical weighting matrix when there is no missing data and satisfies $\overline{W} \geq W$. For example, in the shadowed case, W can be computed by $$W_i = I_i \exp(-g_i) \tag{6}$$

where $I_i$ is the flux for ray i and $g_i$ is the attenuation with shadow. To compute $\overline{W}$, one can use a shadow corrected attenuation $\bar{g}_i$, and the equation becomes $$\overline{W}_i = I_i \exp(-\bar{g}_i). \tag{7}$$

We then compute D by $$\text{Diag}\{D\} = A^t \overline{W} A 1 \tag{8}$$

It is easy to verify that $\overline{W} \geq W$ since $\bar{g}_i \leq g_i$. Therefore, $D \geq D_n$ defined in the first method, so that it also ensures the condition in equation (3) holds.

Figure 6A:
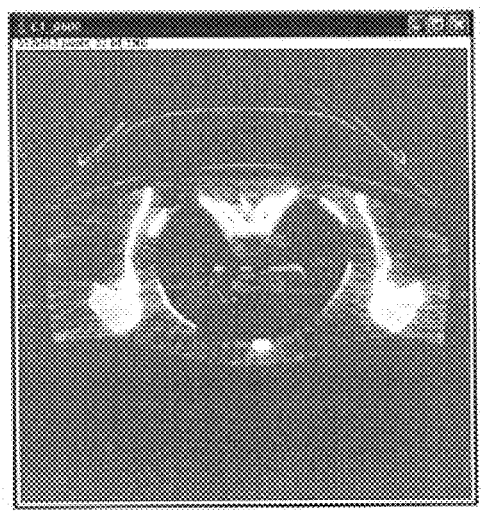
FIG. 6A-7C illustrate reconstructed images.
Figure 6B:
Figure 6C:
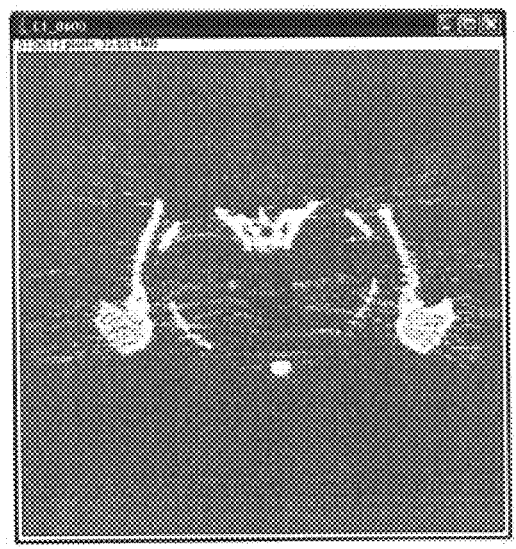

FIGS. 6A, 6B, and 6C illustrate a comparison of with- and without-OS schemes for a bone-like image component. In particular, FIG. 6A illustrates a non-OS reconstruction approach after 600 iterations, while FIG. 6B illustrates a non-OS scheme after 6000 iterations. Finally, FIG. 6C illustrates an OS scheme according to the present embodiments after 600 iterations.

Figure 7A:
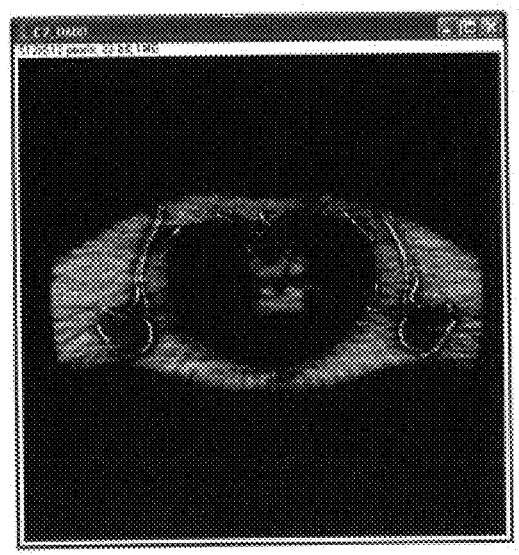
Figure 7B:
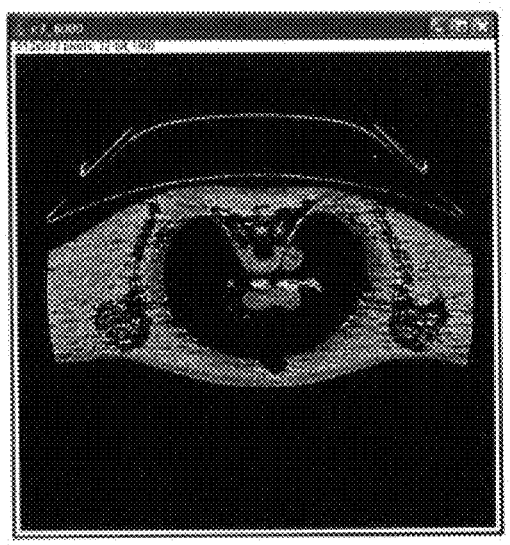
Figure 7C:
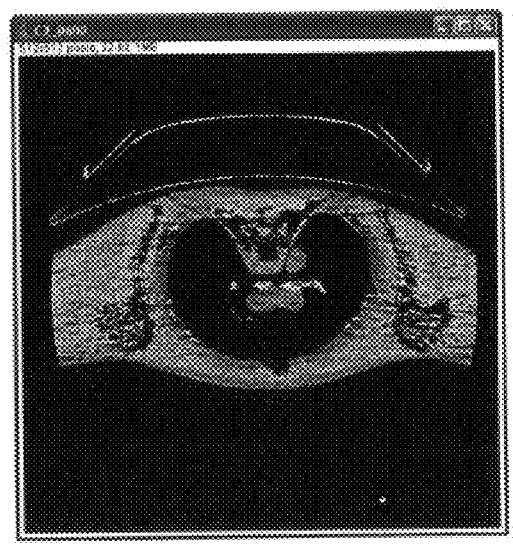

Similarly, FIGS. 7A, 7B, and 7C illustrate a comparison of without- and with-OS schemes for a water-like image component. In particular, FIG. 7A illustrates a non-OS reconstruction approach after 600 iterations, while FIG. 7B illustrates a non-OS scheme after 6000 iterations. Finally, FIG. 7C illustrates an OS scheme according to the present embodiments after 600 iterations.

Figure 8:
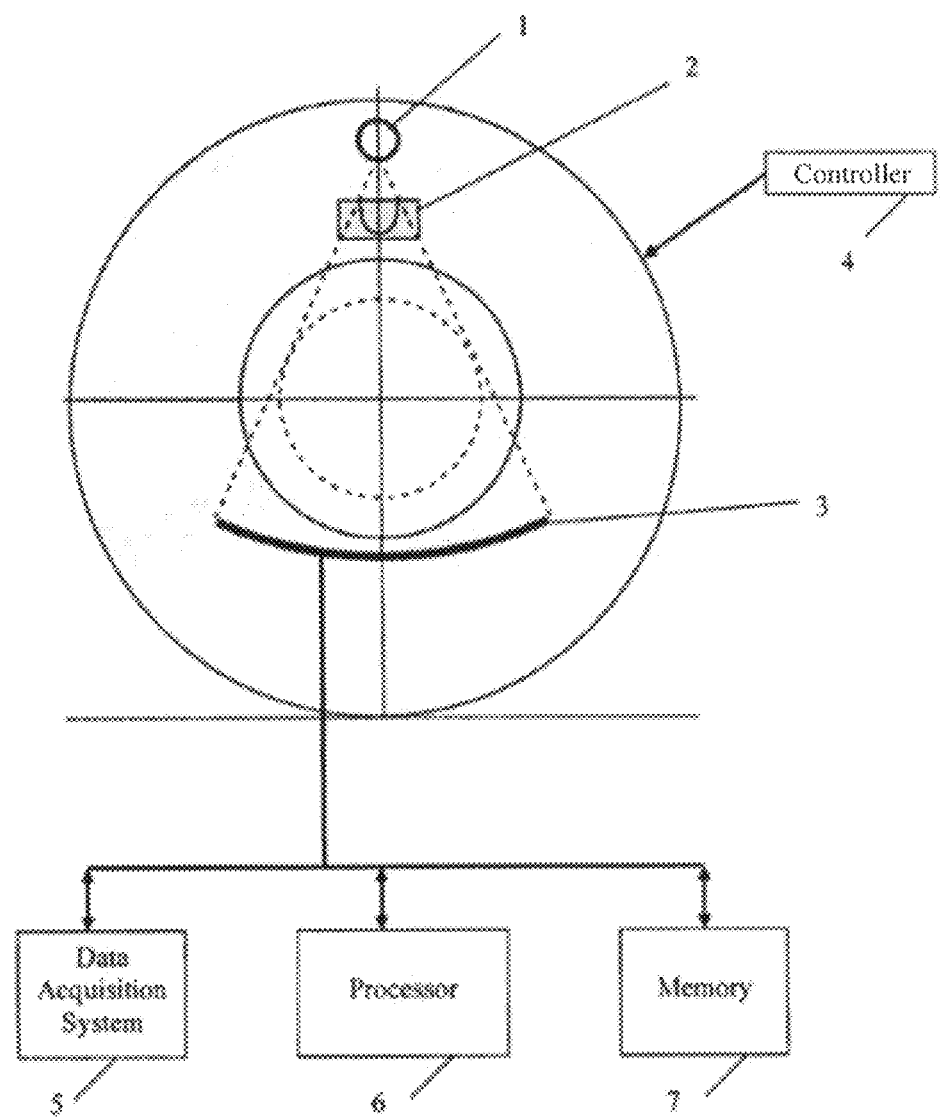
FIG. 8 illustrates a CT scanner system according to the present embodiments.

FIG. 8 illustrates the basic structure of a CT scanner apparatus that includes the detectors described herein. The CT apparatus of FIG. 8 includes an X-ray tube 1, filters and collimators 2, and detector 3. As shown in FIG. 1, the CT apparatus also includes sparse fixed energy-discriminating detectors. The CT apparatus will also include additional mechanical and electrical components such as a gantry motor and a controller 4 to control the rotation of the gantry, control the X-ray source, and control a patient bed. The CT apparatus also includes a data acquisition system 5 and a processor 6 to generate CT images based on the projection (view) data acquired by the data acquisition system. The processor and data acquisition system make use of a memory 7, which is configured to store, e.g., projection data and reconstructed images.

In one embodiment, the spectral computed tomography (CT) scanner apparatus shown in FIGS. 1 and 8 includes a rotating X-ray source 1, a plurality of fixed energy-discriminating detectors; and a processor (e.g., hardware processing circuit such as a CPU) 6 configured/programmed to perform a spectral computed tomography (CT) ordered subsets (OS) reconstruction method using two sets of projection data having a different number of views, the method comprising: (1) obtaining a first set of projection data that includes single-energy CT data for a first number of views; (2) obtaining a second set of projection data that includes spectral CT data for a second number of views, wherein the first and second numbers are integers and the second number is smaller than the first number; (3) partitioning the first set of projection data into N equal-sized subsets of projection data; (4) including the second set of projection data in each of the N subsets of projection data to generate N expanded subsets of projection data; and (5) performing OS reconstruction with the N expanded subsets of projection data to generate a reconstructed CT image.

As one of ordinary skill in the art would recognize, the processor 6 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

Once processed by the pre-reconstruction processor, the processed signals are passed to the reconstruction processor, which is configured to generate CT images. The images are stored in the memory, and/or displayed on a display. As one of ordinary skill in the art would recognize, memory can be a hard disk drive, CD-ROM drive, DVD drive, FLASH drive, RAM, ROM or any other electronic storage known in the art. The display can be implemented as an LCD display, CRT display, plasma display, OLED, LED or any other display known in the art. As such, the descriptions of the memory and the display provided herein are merely exemplary and in no way limit the scope of the present advancements.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An apparatus to perform a spectral computed tomography (CT) ordered subsets (OS) reconstruction method using two sets of projection data having a different number of views, the apparatus comprising:
   a processing circuit configured to
   obtain a first set of projection data that includes single-energy CT data for a first number of views;
   obtain a second set of projection data that includes spectral CT data for a second number of views, wherein the second number is smaller than the first number;
   partition the first set of projection data into N equal-sized subsets of projection data;
   include the second set of projection data in each of the N subsets of projection data to generate N expanded subsets of projection data; and
   perform OS reconstruction with the N expanded subsets of projection data to generate a reconstructed CT image.

2. The apparatus of claim 1, wherein the processing circuit is further configured to:
   perform data domain decomposition on the second set of projection data to obtain measured basis line integrals; and
   initialize basis images.

3. The apparatus of claim 2, wherein, in performing OS reconstruction, the processing circuit is further configured to:
   reproject the basis images to obtain first basis line integrals, and reproject the basis images to obtain second basis line integrals;
   perform beam hardening correction on the first set of projection data to generate corrected data;
   update the basis images with a difference of the measured basis line integrals and the first basis line integrals and a difference of the corrected data and combined second basis line integrals; and
   repeat the reprojecting, performing, and updating steps for the second number of views and for each of the N subsets.

4. The apparatus of claim 3, wherein the processing circuit is further configured to:
   repeat the reprojecting, performing, updating steps, and repeating steps until predetermined convergence criteria is met.

5. The apparatus of claim 1, wherein, in performing the partitioning, the processing circuit is further configured to partition the first set of projection data into N subsets of projection data,
   wherein N is set to be equal to the first number divided by the second number.

6. A spectral computed tomography (CT) ordered subsets (OS) reconstruction method using two sets of projection data having a different number of views, the method comprising:

obtaining a first set of projection data that includes single-energy CT data for a first number of views;

obtaining a second set of projection data that includes spectral CT data for a second number of views, wherein the second number is smaller than the first number;

partitioning the first set of projection data into N equal-sized subsets of projection data;

including the second set of projection data in each of the N subsets of projection data to generate N expanded subsets of projection data; and performing OS reconstruction with the N expanded subsets of projection data to generate a reconstructed CT image.

7. The method of claim 6, further comprising:

performing data domain decomposition on the second set of projection data to obtain measured basis line integrals; and initializing basis images.

8. The method of claim 7, wherein the step of performing OS reconstruction comprises:

reprojecting the basis images to obtain first basis line integrals, and reprojecting the basis images to obtain second basis line integrals;

performing beam hardening correction on the first set of projection data to generate corrected data;

updating the basis images with a difference of the measured basis line integrals and the first basis line integrals and a difference of the corrected data and combined second basis line integrals; and repeating the reprojecting, performing, and updating steps for the second number of views and for each of the N subsets.

9. The method of claim 8, further comprising:

repeating the reprojecting, performing, updating steps, and repeating steps until predetermined convergence criteria is met.

10. The method of claim 6, wherein the partitioning step comprises partitioning the first set of projection data into N subsets of projection data, wherein N is set to be equal to the first number divided by the second number.

11. The method of claim 8, wherein the updating step comprises:

calculating a diagonal denominator matrix $D_n$ for each of the N subsets as $\text{Diag}\{D_n\}=NA^t_n W_n A_n 1$, wherein $A_n$ is a projector matrix, $W_n$ is a weighting matrix, t represents transpose, and 1 is a vector of ones.

12. The method of claim 11, further comprising calculating a global matrix D as $$D_{ii} = \max_n D_{n,ii}.$$

13. The method of claim 8, wherein the updating step comprises:

calculating a diagonal denominator matrix D as $\text{Diag}\{D\}=A^t \tilde{W} A 1$, wherein A is a projector matrix, t represents transpose, and 1 is a vector of ones, and $\tilde{W}$ is a statistical weighting matrix that is calculated as $\tilde{W}_i = I_i \exp(-\tilde{g}_i)$ where $I_i$ is a flux for ray i and $\tilde{g}_i$ is a shadow-corrected attenuation.

* * * * *